ROSE PLANT
Filed May 10, 1973 2 Sheets-Sheet 1
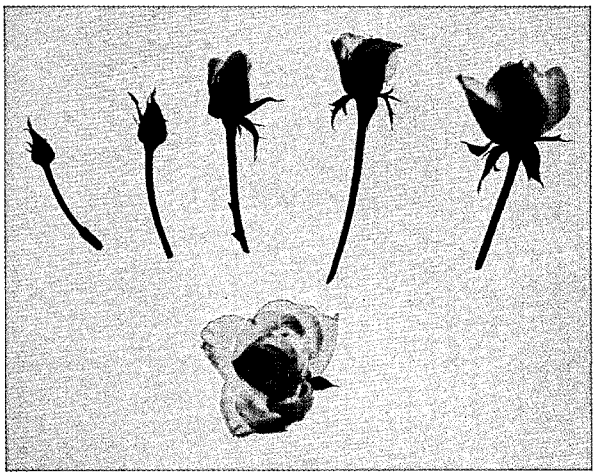
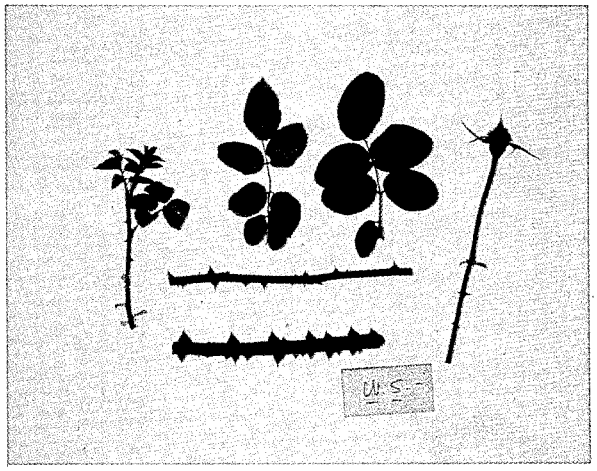

ROSE PLANT
Filed May 10, 1973 2 Sheets-Sheet 2
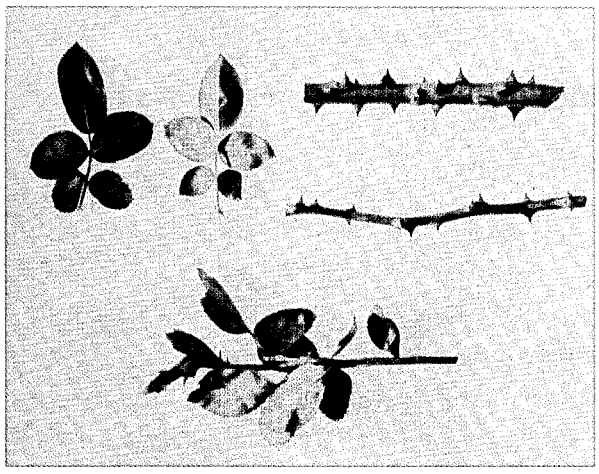

United States Patent Office

Plant Pat. 3,649

Patented Nov. 12, 1974

3,649

ROSE PLANT

Dorothy Jean Searles Bailey, 1101 Lomita Drive, Bakersfield, Calif. 93307

Filed May 10, 1973, Ser. No. 359,096

Int. Cl. A01h 5/00

U.S. Cl. Plt.—14 1 Claim

The present invention relates to a new and distinct variety of rose plant of the Hybrid Tea class. It was originated by me by crossing the rose variety known as "Virgo" with the variety known as "Ivory Fashion" (Plant Patent No. 1,688).

As the result of this breeding, I have produced a new and improved variety which is distinguished from its parents, as well as from all other rose varieties of which I am aware, as evidenced by the unique combination of characteristics which are outstanding therein:

(1) A neat, moderately vigorous upright bush of typical Hybrid Tea habit;

(2) Medium large, Dark Green foliage that abundantly covers the plant;

(3) Abundant bloom production from early spring until fall, especially during the warmest periods;

(4) Flowers borne singly to each stem, the stems being strong, medium long;

(5) Thick velvety petals that do not spot pink or brown or bruise easily;

(6) Urn shaped bud, 1¼–1½ inches long, that slowly opens into a high-centered bloom of very regular petal conformation;

(7) Clean white color of petals that shades into Naples Yellow 403/3 at the base; and (8) A slight clean Sweetbriar fragrance.

In comparison with the parent varieties, this new variety has inherited the habit of its maternal parent, "Virgo," both having moderate vigor, upright bush, typical Hybrid Tea habit, and medium sized dark green foliage. The paternal parent, "Ivory Fashion," has contributed increased mildew resistance to the new variety and harder foliage, compared to "Virgo," "Virgo" is a clear white under ideal conditions, but more often is spotted with pink and bruises moderately easily. "Ivory Fashion" is a smooth ivory in the range of Naples Yellow 403/3, but with thicker petals, more resistant to spotting and bruising. The new variety is a clear white shading into Naples Yellow 403%3 toward the base. The thick, clean petals with the absence of spotting and resistance to bruising has been inherited by the new variety from "Ivory Fashion," and is an important characteristic for white roses. The bloom of "Ivory Fashion" is small but high-centered and of very regular conformation, having a fine small urn-shaped bud. "Virgo" has a larger bud and a nice high centered bloom. The new variety has inherited the bud and bloom size from "Virgo," and the improved bud and bloom form from "Ivory Fashion."

The accompanying photographs show typical specimens of the vegetative growth and flowers of my new variety in different stages of development and are depicted in color as nearly true as it is reasonably possible with color photography.

The following is a detailed description of my new variety, with color terminology in accordance with the Horticultural Colour Chart of the British Colour Council, except where general color terms of ordinary dictionary significance are obvious, as based upon observations of specimens grown at Shafter, California:

Type: Half-hardy; bush, upright, greenhouse, outdoor; seedling; for cut flowers, garden decoration.

Class: Hybrid Tea.

Breeding: Seedling. Seed Parent—"Virgo." Pollen Parent—"Ivory Fashion." Date of Sowing—1964. When first asexually reproduced—1967. First asexual reproduction made at Shafter, California, by means of budding.

Propogation: Holds its distinguishing characteristics through succeeding propogations.

FLOWER

Continuity: Continuous.

Fragrance: Slight, sweetbriar.

Flowers Borne: Singly, several to stem; strong, medium and long stems.

Quantity of Bloom: Free, abundant outdoor, in greenhouse.

Bud:

*Peduncle.*—Medium long; medium heavy; reddish; numerous green hairs.

*Before calyx breaks.*—Size—Medium large. Form—Long, pointed, with a conspicuous neck; without foliaceous appendages on the surface of the bud. Color—Pod Green 061/2 with Erythrite Red 0027/2.

*As calyx breaks:* Color—No significant change.

*As first petal opens:* Size—Medium large. Form—Ovoid. Color—Outside: White, base Naples Yellow, slightly lighter than 403/3. Inside: White, base Naples Yellow, slightly lighter than 403/3. Opening—It does open up well. It is retarded by cold, wet weather.

Bloom:

*Size.*—When fully open, 4 to 5 inches.

*Petalage.*—Very double; 25 to 30 petals.

*Form.*—High centered; petals being at first loosely rolled outward; becoming at maturity loosely rolled outward.

Petals:

*Texture.*—Thick; with inside velvety; with outside shiny.

*Shape.*—Outside—oval. Intermediate—ovate. Inside—oval.

This description was made from a rose grown outdoors, August, 1971, Shafter, California.

*Color.*—Outside petal: Outside surface—White, base Naples Yellow, slightly lighter than 403/3. Inside surface—White. Intermediate petal: Outside surface—White, base Naples Yellow, slightly lighter than 403/3. Inside surface—White. Inner petal: Outside surface—White, base Naples Yellow 403/. 3. Inside surface—White, base Naples Yellow, slightly lighter than 403/3.

This description was made from a rose that was open for three days, outdoors, August, 1971, Shafter, California.

*Color.*—Outside petal: Outside surface—White, base Naples Yellow, appreciably lighter than 403/3. Inside surface—White. Inside petal: Outside surface—White, base Naples Yellow, appreciably lighter than 403/3. Inside surface—White, base Naples Yellow 403/4.

*General color effect.*—Newly opened flower—White. Three days open—White.

*Behavior.*—Persisted; fading brownish yellow.

*Flower longevity.*—Bush in garden, 5 days in August; Cut roses grown outdoors, kept at living room temperatures, 3 days in August. Cut roses grown in greenhouse, kept at living room temperatures, 4 days in April.

REPRODUCTIVE ORGANS

Stamens: Arranged regularly. Color—Very Light Yellow.

Filaments: Medium; yellow; most with anthers.

Anthers: Medium; yellow; open at various times.

Pollen: Moderate; yellow
Pistils: Many.
Styles: Uneven; medium long; medium; bunched.
Stigma: Yellow.
Ovaries: All enclosed in calyx.
Hips: None observed.
Sepals: Permanent; long; straight, spear-shaped. Color—persisting brown.
Seeds: None observed.

PLANT

Foliage: Leaves compound of 5 and 7; abundant; medium large; moderately heavy.

*Leaflets.*—Ovoid; mucronate apex; base round; margin simply serrate.

*Color.*—Mature: Upper surface—Dark green. Under surface—Grey-green. Young: Upper surface—Light Green-Red. Under surface—Light Green-Red.

*Rachis* (the supporting stem of the compound leaf).—Medium heavy in thickness. Upper side—Smooth. Under side—Sparsely thorny.

*Stipules.*—Moderately short; moderately wide; short points; turning out at an angle of less than 45°.

*Diseases and Insect Resistance.*—Fair to average mildew and rust resistance.

Growth:

*Habit.*—Upright; many branches.

*Growth.*—Moderately vigorous.

*Canes.*—Moderately heavy.

*Main stems.*—Green. Thorns—several; medium long, straight; with long, narrow base. Prickles—None. Hairs—None.

*Branches.*—Bright green. Thorns—Several, medium long; straight; with long, narrow base. Prickles—Few; reddish. Hairs—Few, reddish.

*New Shoots.*—Bright Green-Red. Thorns—Several; straight; with long, narrow base. Prickles—Few, reddish. Hairs—Few; reddish; glandular.

I claim:

1. A new and distinct variety of rose plant of the Hybrid Tea class, substantially as herein shown and described, characterized particularly as to novelty by the unique combination of a neat upright plant, moderately vigorous of typical Hybrid Tea habit; medium large, Dark Green foliage that abundantly covers the plant; abundant bloom production from early spring until fall, especially during the warmest periods; flowers usually borne singly to each stem, the stems being strong and long; thick velvety petals that have good resistance to spotting and bruising; urn shaped large buds that slowly open into large high-centered blooms of very regular petal conformation; clean white petal color that shades into Naples Yellow 403/3 and lighter at the base; and a slight clear Sweetbriar fragrance.

No references cited.

ROBERT E. BAGWILL, Primary Examiner